United States Patent
Håkansson

(10) Patent No.: US 6,696,964 B1
(45) Date of Patent: Feb. 24, 2004

(54) DEVICE FOR MONITORING THE FILLING OF A BAG

(75) Inventor: Ola Håkansson, Lund (SE)

(73) Assignee: Crafcare AB, Malmo (SE)

( * ) Notice: Subject to any disclaimer, the term of this patent is extended or adjusted under 35 U.S.C. 154(b) by 197 days.

(21) Appl. No.: 10/049,122
(22) PCT Filed: Aug. 24, 2000
(86) PCT No.: PCT/SE00/01624
§ 371 (c)(1), (2), (4) Date: Feb. 6, 2002
(87) PCT Pub. No.: WO01/13830
PCT Pub. Date: Mar. 1, 2001

(30) Foreign Application Priority Data

Aug. 24, 1999 (SE) .............................................. 9902978

(51) Int. Cl.[7] .............................................. G08B 21/00
(52) U.S. Cl. ..................... 340/614; 340/618; 340/626; 340/603; 141/94; 338/34; 338/36; 338/80; 338/231; 73/862.381
(58) Field of Search ................................ 340/614, 603, 340/618; 383/34, 36, 80, 231; 141/18, 94, 311 R; 338/34, 36, 80, 231; 73/862.381; D21/439, 440

(56) References Cited

U.S. PATENT DOCUMENTS

| 2,420,148 | A | | 5/1947 | Ostergren ..................... 338/36 |
| 3,546,944 | A | | 12/1970 | Mack ........................... 73/388 |
| 5,121,107 | A | | 6/1992 | Newell ........................ 340/618 |
| 5,135,485 | A | * | 8/1992 | Cohen et al. ................. 604/67 |
| 5,157,372 | A | | 10/1992 | Langford .................... 338/211 |
| 5,260,692 | A | | 11/1993 | Claren ........................ 340/614 |

FOREIGN PATENT DOCUMENTS

| EP | 0 130 670 | 1/1985 |
| WO | WO94/15190 | 6/1994 |

* cited by examiner

Primary Examiner—Jeffery Hofsass
Assistant Examiner—Jennifer Stone
(74) Attorney, Agent, or Firm—Merchant & Gould, P.C.

(57) ABSTRACT

A device for monitoring the filling of a bag (10) comprises a resistor element to be mounted on the outside surface of the bag, the resistor element being a flexible potentiometer (20), the resistance whereof being changed by bending of the potentiometer due to increasing bulging of the bag wall under continuing filling of the bag. The flexible potentiometer can be connected to an alarm device (24) reacting at a predetermined resistance value of the resistor element.

7 Claims, 3 Drawing Sheets

DEVICE FOR MONITORING THE FILLING OF A BAG

BACKGROUND OF THE INVENTION

The invention relates to a device for monitoring the filling of a bag, comprising a resistor element to be attached to the outside surface of the bag said resistor element having an electric resistance changing by the shape change of the bag during filling thereof, to be connected to an alarm device responding to a predetermined resistance value of the resistor element.

A monitoring device of this kind is described in SE-B-466 381.

The prior art device comprises an electric resistor element the electric resistance of which changes by stretching of the element which is mounted over an extendable portion of the bag wall. The resistor element is stretched elastically manually and is then mounted to the outside surface of the bag. When it is then released it contracts forming a fold or a wrinkled or folded portion of the bag wall. As the bag is filled the fold or the wrinkled or folded portion will be smoothed down under elastic stretching of the resistor element and thus successive change of the resistance thereof. At a predetermined resistance value alarm is given by the alarm device. Said predetermined resistance value should be at such level that alarm is given when the bag is filled or nearly filled.

The resistor element of the prior art device can be stretched to a varying degree when being mounted to the bag, which means that the resistance value of the resistor element is not under complete control at mounting to the empty bag and thus it cannot be assured that said predetermined resistance value will be attained when the bag is filled. Moreover, not all bags are of such nature that the bag wall after mounting of the resistor element forms a fold or a wrinkled or folded portion under said element, which will be smoothed down under filling of the bag in order that the resistor element shall provide a reliable indication of the filling degree of the bag. Also the possible ageing or fatigue of the resistor element by repeated use has to be taken into account jeopardizing the intended purpose of the monitoring device.

SUMMARY OF THE INVENTION

The object of the invention is to provide a device for monitoring the filling of a bag, which provides a more reliable sensing of the filling degree of the bag because the mounting of the resistor element on the bag includes no manual step which may cause a non-desired variation in the initial resistance of the resistor element and thus uncertainty of the relation between the resistance value and the filling degree of the bag. It is also an object to provide a device of the kind referred to which can be used on bags of any existing type in order to provide reliable monitoring of the filling of the bag and which can easily be mounted to the bag and additionally is of a simple construction.

In order to achieve these and other objects which will be apparent from the description which follows the invention provides a device of the kind referred to having the characterizing features set forth in claim 1.

The device of the invention can be used on any drainage bag used in the medical care but is proposed in the first place for use on stomi bags in order to give an alarm when the stomi bag is full but not yet so full that there is a risk of the bag will come off the user's body where it is attached by tape over the stoma, which would of course involve great discomfort for the user. However, the device can be used also in the industry for monitoring the collection of liquids of different kinds, for example the collection of condensate from dehumidifiers.

BRIEF DESCRIPTION OF THE DRAWINGS

In order to explain the invention in more detail illustrative embodiments thereof will be described below in connection with a stomi bag reference being made to the accompanying drawings in which.

DETAILED DESCRIPTION OF THE DRAWINGS

Figure 1:
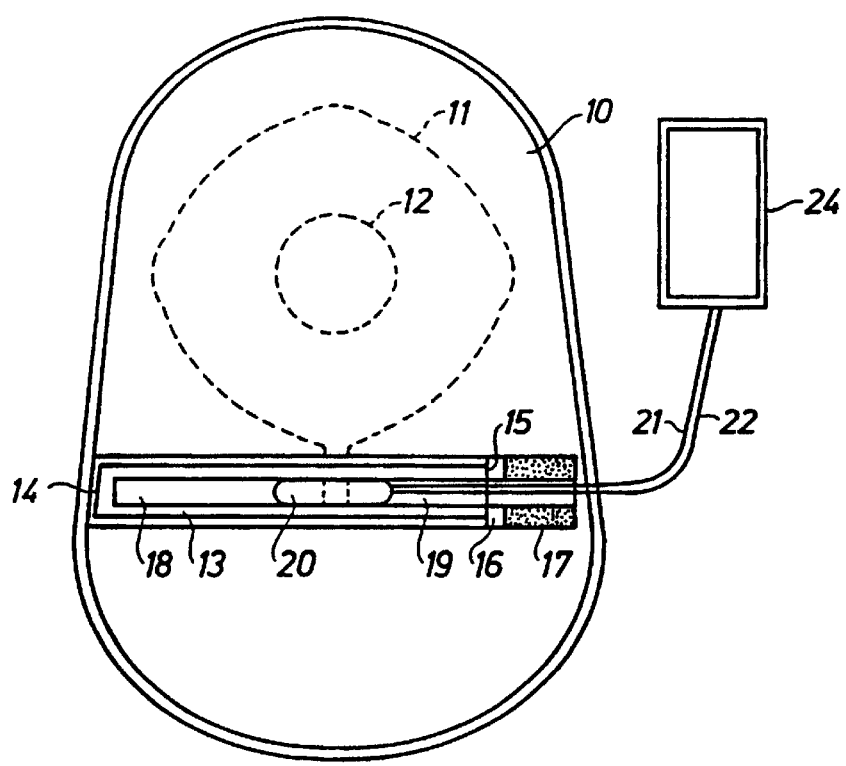
FIG. 1 is a plan view of a flattened stomi bag provided with the monitoring device according to the invention in a first embodiment thereof.
Figure 2:
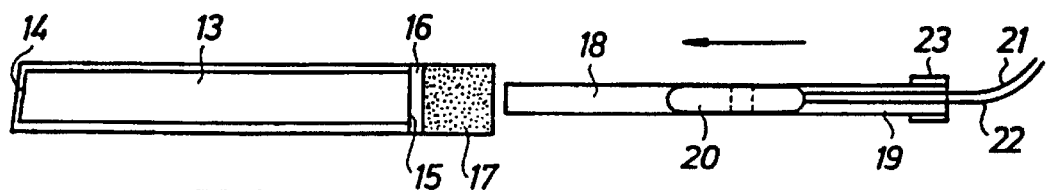
FIG. 2 is a plan view of the monitoring device with the parts thereof in exploded position.

FIG. 1 in the drawing shows a stomi bandage which comprises a stomi bag 10 of plastic foil or another suitable liquid proof material, which in FIG. 1 is shown in a flattened condition and at one side thereof (the back side) has an adhesive plaster 11 which surrounds an inlet opening 12. The stomi bag shall be attached to the user's body by means of the adhesive plaster with the inlet opening 12 registering with the user's stomi opening. At the other side (the front side) of the flattened stomi bag a pocket 13 of plastic foil is attached which is closed at one end 14 thereof and is open at the other end 15 thereof. The pocket 13 can have a self-adhesive surface by means of which it is demountably attached to the stomi bag. On a flap 16 projecting from the open end 15 a piece of Velcro tape 17 is attached.

A transducer comprises two rigid rails 18 and 19, for example of plastic, which are hingedly interconnected by means of a resistor element 20 or by means of a plastic foil on which the resistor element is mounted so that the rails can be angled in relation to each other under bending of the resistor element. According to the invention this element shall comprise a flexible potentiometer of the kind described in U.S. Pat. No. 5,157,372. Such a potentiometer is marketed under the trade mark Bend Sensor® by Flexpoint Inc., Midvale, Utah 84047, USA, and comprises a thin film for example a plastic film of polyester or polyamide, and a varnish layer of a resistor material applied to said film. At bending of the coated film said resistor material forms micro cracks which at repeated bending are opened and closed changing the resistance of the layer. The relation between the resistance and bending follows one and the same characteristic at repeated bending of the flexible potentiometer. Conductor wires 21 and 22 are connected to the flexible potentiometer with the potentiometer connected in series between the wires. On the lower side of the rail 19 a Velcro tape 23 is attached for co-operation with the Velcro tape 17. The Velcro tapes can be replaced by double adhesive tape.

Figure 3:
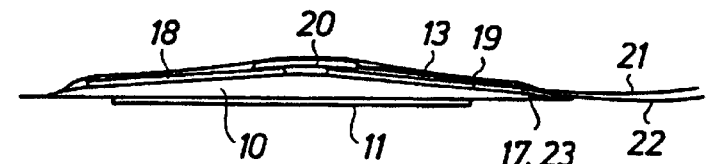
FIG. 3 is an end view of the stomi bag with the monitoring device in substantially empty condition.
Figure 4:
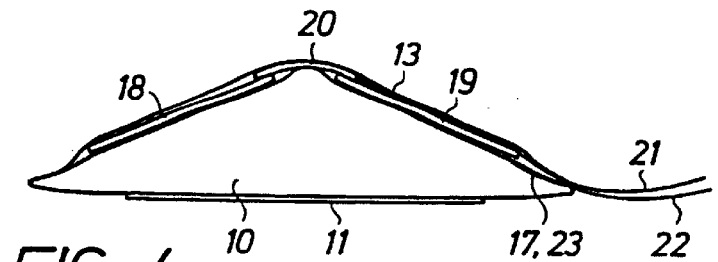
FIG. 4 is a corresponding end view of the stomi bag in filled condition.

When the pocket 13 at the self-adhesive surface has been attached to the stomi bag 10 as shown in FIG. 1 the transducer formed by the rails 18 and 19 and the flexible potentiometer 20 is pushed into the pocket at the open end 15 thereof. The Velcro tape 23 then will be located opposite to the Velcro tape 17 and is attached in this position by the tapes being pressed against each other and as a consequence thereof releasable engage with each other. The conductor wires 21 and 22 are connected to an electric circuit in an alarm box 24. In dependence of a predetermined resistance value in the flexible potentiometer the electric circuit shall activate an alarm device provided in the alarm box. When the bag is flattened, FIGS. 1 and 3, the alarm device is deactivated. As the stomi bag is being filled the wall thereof will bulge the two rails 18 and 19 being angled in relation to each other, FIG. 4, so that the resistance of the flexible potentiometer is changed. At the predetermined resistance value, corresponding to a bulging of the bag wall, which in turn corresponds to a certain filling degree, for example a well filled but not too full stomi bag, the electric circuit activates the alarm device so that the user's attention is drawn to the fact that it is time to exchange the stomi bag and that this can be done before the stomi bag is so full that there is a risk that it comes off the location in connection with the stomi opening with the discomfort that would be connected there with. The alarm can be given as sound, light or vibration which is directed towards the user's skin. If the user is not able to exchange the stomi bag himself when it is full due to an existing illness or due to the fact that the user is a small child, the flexible potentiometer can be connected with an existing alarm system and give a signal to this system for giving an alarm for the attention of a nurse or another capable person.

Another possibility is to provide a wireless connection between the flexible potentiometer 20 and the alarm box 24 which then can be located with another person than the user of the stomi bag. A chip with a radio transmitter and power source can be connected with the transducer formed by the rails 18 and 19 and the flexible potentiometer 20 and can be activated when the transducer is mounted in the plastic pocket. The transmitter transmits a signal for activating the alarm device at the predetermined resistance value of the flexible potentiometer. In the Velcro tape 17 or 23 there can in that case be provided a switch which normally is open but will be closed for connecting the transmitter controlled by the potentiometer, when the Velcro tapes are interconnected.

The pocket 13 which is attached to the stomi bag, and the flexible potentiometer 20 shall be intended for use several times, and one pocket can be provided for each set of a predetermined number, for example ten, stomi bags while the flexible potentiometer including the rails 18 and 19 can be used considerable more times before it has to be exchanged.

Figure 5:
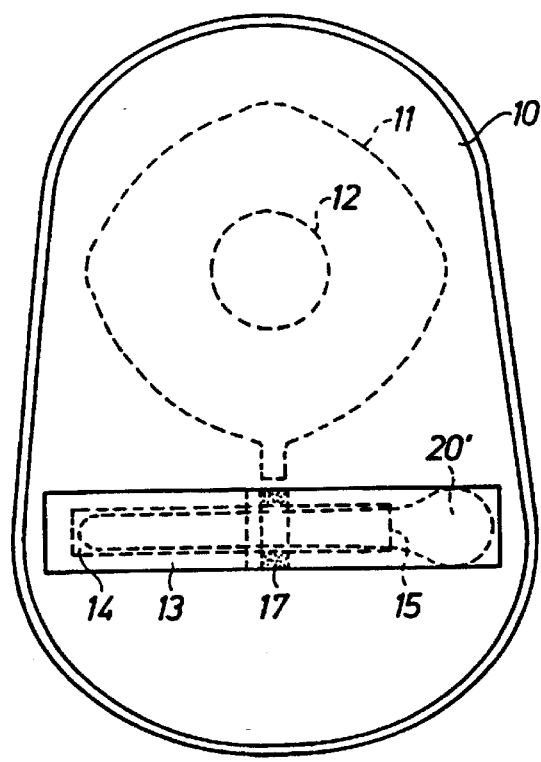
FIG. 5 is a corresponding view as FIG. 1 of a second embodiment of the invention.
Figure 6:
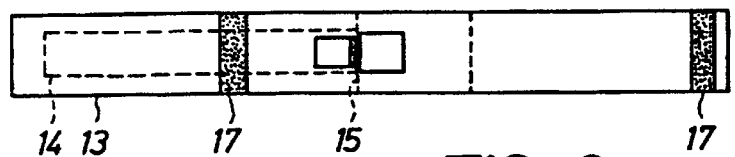
FIG. 6 is a plan view of a pocket for attachment to the stomi bag.
Figure 7:
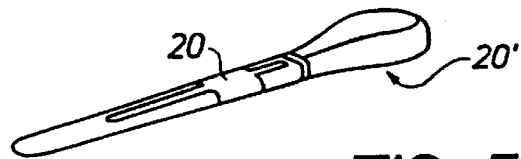
FIG. 7 is a perspective view of a measurement stick for insertion in the pocket.

An embodiment of the invention with functional similarities with the one shown in FIGS. 1–4 is disclosed in FIGS. 5–7. A pocket 13, shown in an open condition in FIG. 6 and having a closed end 14 and an open end 15, is attached to the stomi bag 10, for example by a self-adhesive surface.

A transducer or measurement stick 20' for insertion in the pocket 13 is shown in FIG. 7. In its thicker portion to the right in FIG. 7 the stick is provided with electronic means (including a battery) for handling a signal from the resistor element 20 and sireless transmission thereof to an external alarm device (not shown).

The resistor element 20 constitutes a flexible portion of the stick 20', which accordingly is bent at the bulging of the bag.

As in the embodiment of FIGS. 1–4, the pocket 13 for the measurement stick 20' has a flap 16 projecting from the open end 15 and pieces of Velcro tape 17 for its closure over the stick.

Figure 8:
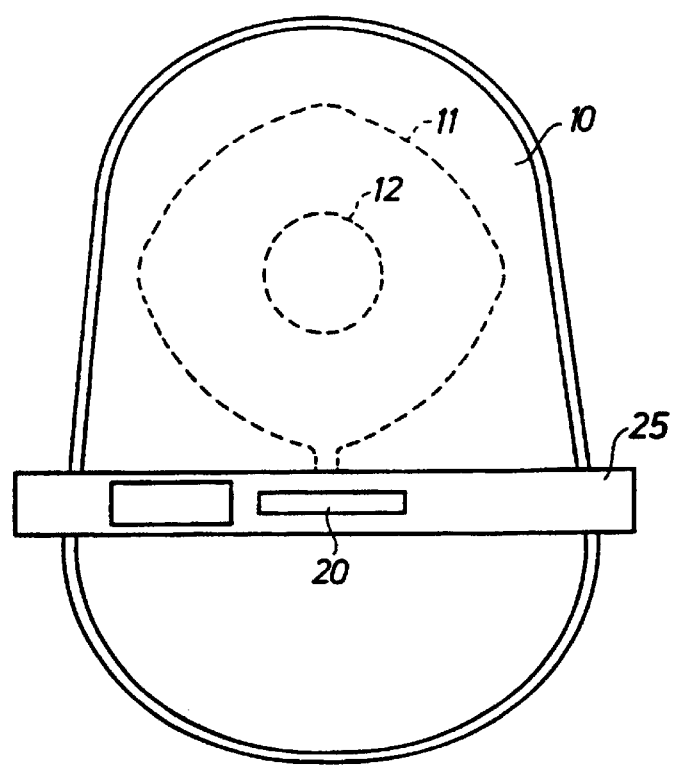
FIG. 8 is a corresponding view as FIG. 1 of a third embodiment of the invention.
Figure 9:
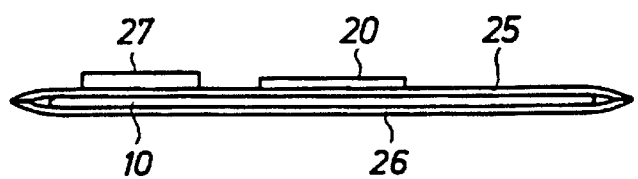
FIG. 9 is an end view of the embodiment in FIG. 5 with the stomi bag flattened.
Figure 10:
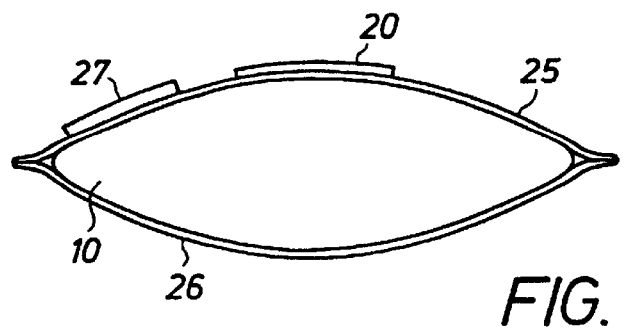
FIG. 10 is an end view corresponding to FIG. 6 with the stomi bag filled.

Instead of the transducer formed by the rails 18 and 19 and the flexible potentiometer 20 being pushed into a pocket as in the embodiments described, the flexible potentiometer can be mounted to one side or the other of a rail 25 according to the embodiment of the invention disclosed in FIGS. 8 to 10. The rail 25 is connected at the ends thereof with the ends of another rail 26. The monitoring device 26 is mounted to the stomi bag 10 by the monitoring device being inserted between the rails which, when the bag is flattened, FIG. 9., lies substantially flat against the bag but will be bent as the bag is being filled, FIG. 10. The rails must, of course, be sufficiently thin and easily bendable in order to stand the bulging of the bag at the filling thereof. For wireless alarm via the flexible potentiometer 20 in the manner described above a transmitter 27 is provided on the rail 25, but alternatively the flexible potentiometer can be connected to an electric circuit in an alarm box by means of wires.

In the illustrative embodiments described a single flexible potentiometer is provided but it is within the scope of the invention to provide two or more such potentiometers in order to create a more reliable alarm system.

What is claimed is:

1. Device for monitoring the filling of a bag 10 comprising a resistor element to be mounted on the outside surface of the bag said resistor element having an electric resistance which changes by the shape change of the bag during filling thereof and can be connected to an alarm device (24) reacting at a predetermined resistance value of the resistor element, characterized in that the resistor element comprises a flexible potentiometer (20), the resistance whereof being changed by bending of the potentiometer due to increasing bulging of the bag wall under continuing filling of the bag (10).

2. Device according to claim 1 wherein the flexible potentiometer (20) is constructed as a hinge between two rigid rails (18, 19) to be bent at angling of the rails in relation to each other.

3. Device according to claim 2 wherein the flexible potentiometer (20) and the rails (18, 19) are inserted into a pocket (13) of flexible material mounted to the bag (10) preferably exchangeably mounted.

4. Device according to claim 3, wherein at least one (19) of the rails is demountably fixed in the pocket (13).

5. Device according to claim 4, wherein the demountable connection between said one rail (19) and the pocket (13) is provided by means of Velcro tapes (17, 13) doubleadhesive tape or the like.

6. Device according to claim 1 wherein the flexible potentiometer (20) is provided on a flexible rail (25) which at the ends thereof is connected with another flexible rail (26) the bag (10) being inserted between the rails in order that the rails shall follow from substantially flat condition with the bag flattened the bulging of the bag at filling thereof.

7. Device according to claim 1 wherein conductor wires (21, 22) connected with the flexible potentiometer (20) are connectable with the alarm device (24) with the potentiometer connected in series between the conductor wires.

* * * * *